US008900315B2

(12) United States Patent
Lipman et al.

(10) Patent No.: US 8,900,315 B2
(45) Date of Patent: Dec. 2, 2014

(54) CONSTRAINED CONDYLAR KNEE DEVICE

(75) Inventors: Joseph D. Lipman, New York, NY (US);
Donald L. Bartel, Ithaca, NY (US);
Timothy M. Wright, New York, NY
(US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 0 days.

(21) Appl. No.: 12/947,474

(22) Filed: Nov. 16, 2010

(65) Prior Publication Data

US 2011/0125279 A1    May 26, 2011

Related U.S. Application Data

(60) Provisional application No. 61/281,362, filed on Nov. 16, 2009.

(51) Int. Cl.
*A61F 2/38* (2006.01)
*A61F 2/30* (2006.01)

(52) U.S. Cl.
CPC ............... *A61F 2/3886* (2013.01); *A61F 2/389* (2013.01); *A61F 2/3859* (2013.01); *A61F 2002/30301* (2013.01)
USPC ..................................................... 623/20.26

(58) Field of Classification Search
CPC ...... A61F 2/3886; A61F 2/3859; A61F 2/389
USPC ........................ 623/20.14, 20.15, 20.25–20.36
See application file for complete search history.

(56) References Cited

U.S. PATENT DOCUMENTS

| | | | | |
|---|---|---|---|---|
| 3,748,662 | A * | 7/1973 | Helfet | 623/20.31 |
| 4,209,861 | A * | 7/1980 | Walker et al. | 623/20.27 |
| 4,309,778 | A * | 1/1982 | Buechel et al. | 623/20.29 |
| 4,634,444 | A * | 1/1987 | Noiles | 623/20.27 |
| 5,007,933 | A * | 4/1991 | Sidebotham et al. | 623/20.27 |
| 5,116,375 | A * | 5/1992 | Hofmann | 623/20.27 |
| 5,133,758 | A * | 7/1992 | Hollister | 623/20.31 |
| 5,147,405 | A * | 9/1992 | Van Zile et al. | 623/20.27 |
| 5,282,869 | A * | 2/1994 | Miyajima et al. | 623/20.27 |
| 5,282,870 | A * | 2/1994 | Moser et al. | 623/20.31 |
| 5,326,361 | A * | 7/1994 | Hollister | 623/20.31 |
| 5,330,534 | A * | 7/1994 | Herrington et al. | 623/20.27 |
| 5,370,699 | A * | 12/1994 | Hood et al. | 623/20.28 |
| 5,549,686 | A * | 8/1996 | Johnson et al. | 623/20.27 |
| 5,609,643 | A * | 3/1997 | Colleran et al. | 623/20.29 |
| 5,782,921 | A * | 7/1998 | Colleran et al. | 623/20.15 |
| 5,824,100 | A * | 10/1998 | Kester et al. | 623/20.31 |

(Continued)

*Primary Examiner* — Alvin Stewart
(74) *Attorney, Agent, or Firm* — Leason Ellis LLP

(57) ABSTRACT

A knee joint prosthesis includes a femoral component having a first condylar bearing surface and a second condylar bearing surface. Each of the first and second condylar bearing surfaces has a cross-section in a coronal plane that exhibits at least two different radii. The prosthesis also includes a tibial component and an insert component associated with the tibial component. The insert component has bearing surfaces that are complementary to the first and second condylar bearing surfaces, wherein a contact point is established between the bearing surfaces of the insert component and the first and second condylar bearing surface. In accordance with the present invention and as a result of the above construction, varus and valgus rotation of the femoral component relative to the insert component causes the contact point to move laterally as the knee is rotated. By shifting the contact pointy laterally/outwardly, the knee stability (i.e., stiffness) gradually increased.

17 Claims, 20 Drawing Sheets

(56) References Cited

U.S. PATENT DOCUMENTS

| | | | |
|---|---|---|---|
| 5,871,539 A * | 2/1999 | Pappas | 623/20.31 |
| 5,871,546 A * | 2/1999 | Colleran et al. | 623/20.28 |
| 5,935,173 A * | 8/1999 | Roger et al. | 623/20.31 |
| 6,152,960 A * | 11/2000 | Pappas | 623/20.31 |
| 6,165,223 A * | 12/2000 | Metzger et al. | 623/20.27 |
| 6,168,629 B1 * | 1/2001 | Timoteo | 623/20.27 |
| 6,203,576 B1 * | 3/2001 | Afriat et al. | 623/20.27 |
| 6,206,926 B1 * | 3/2001 | Pappas | 623/20.27 |
| 6,235,060 B1 * | 5/2001 | Kubein-Meesenburg et al. | 623/20.31 |
| 6,406,497 B2 * | 6/2002 | Takei | 623/20.31 |
| 6,413,279 B1 * | 7/2002 | Metzger et al. | 623/20.29 |
| 6,416,552 B1 * | 7/2002 | Hoeppner et al. | 623/20.15 |
| 6,443,991 B1 * | 9/2002 | Running | 623/20.27 |
| 6,458,160 B2 * | 10/2002 | Biegun et al. | 623/20.27 |
| 6,491,726 B2 * | 12/2002 | Pappas | 623/20.29 |
| 6,558,427 B2 * | 5/2003 | Leclercq et al. | 623/20.33 |
| 6,699,291 B1 * | 3/2004 | Augoyard et al. | 623/20.27 |
| 6,726,723 B2 * | 4/2004 | Running | 623/20.27 |
| 6,730,128 B2 * | 5/2004 | Burstein | 623/20.27 |
| 6,764,516 B2 * | 7/2004 | Pappas | 623/20.29 |
| 6,770,097 B2 * | 8/2004 | Leclercq | 623/20.15 |
| 6,797,005 B2 * | 9/2004 | Pappas | 623/20.27 |
| 6,902,582 B2 * | 6/2005 | Kubein-Meesenburg et al. | 623/20.31 |
| 6,972,039 B2 * | 12/2005 | Metzger et al. | 623/20.29 |
| 7,081,137 B1 * | 7/2006 | Servidio | 623/20.14 |
| 7,160,330 B2 * | 1/2007 | Axelson et al. | 623/20.14 |
| 7,261,740 B2 * | 8/2007 | Tuttle et al. | 623/20.32 |
| 7,326,252 B2 * | 2/2008 | Otto et al. | 623/20.15 |
| 7,413,577 B1 * | 8/2008 | Servidio | 623/20.14 |
| 7,422,605 B2 * | 9/2008 | Burstein et al. | 623/20.33 |
| 7,678,152 B2 * | 3/2010 | Suguro et al. | 623/20.27 |
| 7,837,737 B2 * | 11/2010 | Hedley et al. | 623/20.35 |
| 7,875,081 B2 * | 1/2011 | Lipman et al. | 623/20.27 |
| 7,896,924 B1 * | 3/2011 | Servidio | 623/20.3 |
| 7,922,771 B2 * | 4/2011 | Otto et al. | 623/20.31 |
| 7,938,862 B2 * | 5/2011 | Naegerl | 623/20.21 |
| 7,955,394 B2 * | 6/2011 | Hotokebuchi et al. | 623/20.14 |
| 7,981,159 B2 * | 7/2011 | Williams et al. | 623/20.21 |
| 8,075,626 B2 * | 12/2011 | Dun | 623/20.27 |
| 8,211,181 B2 * | 7/2012 | Walker | 623/20.21 |
| 8,382,845 B2 * | 2/2013 | Metzger et al. | 623/20.21 |
| 8,409,293 B1 * | 4/2013 | Howard et al. | 623/20.15 |
| 8,721,733 B2 * | 5/2014 | Bonitati | 623/23.46 |
| 2001/0034555 A1 * | 10/2001 | Pappas | 623/20.29 |
| 2002/0010512 A1 * | 1/2002 | Takei | 623/20.31 |
| 2003/0004577 A1 * | 1/2003 | Running | 623/20.27 |
| 2003/0009232 A1 * | 1/2003 | Metzger et al. | 623/20.29 |
| 2004/0122522 A1 * | 6/2004 | Kubein-Meesenburg et al. | 623/20.31 |
| 2004/0143339 A1 * | 7/2004 | Axelson et al. | 623/20.21 |
| 2005/0055102 A1 * | 3/2005 | Tornier et al. | 623/20.32 |
| 2007/0162143 A1 * | 7/2007 | Wasielewski | 623/20.14 |
| 2007/0239281 A1 * | 10/2007 | Gotte et al. | 623/20.27 |
| 2008/0097615 A1 * | 4/2008 | Lipman et al. | 623/20.27 |
| 2009/0043395 A1 * | 2/2009 | Hotokebuchi et al. | 623/20.29 |
| 2009/0048680 A1 * | 2/2009 | Naegerl | 623/20.14 |
| 2009/0204221 A1 * | 8/2009 | Walker | 623/20.27 |
| 2009/0319047 A1 * | 12/2009 | Walker | 623/20.15 |
| 2009/0326663 A1 * | 12/2009 | Dun | 623/20.21 |
| 2009/0326666 A1 * | 12/2009 | Wyss et al. | 623/20.29 |
| 2010/0016979 A1 * | 1/2010 | Wyss et al. | 623/20.27 |
| 2010/0042224 A1 * | 2/2010 | Otto et al. | 623/20.27 |
| 2010/0161067 A1 * | 6/2010 | Saleh et al. | 623/20.31 |
| 2010/0249940 A1 * | 9/2010 | Sanford | 623/20.27 |
| 2011/0066246 A1 * | 3/2011 | Ries et al. | 623/20.27 |
| 2011/0118847 A1 * | 5/2011 | Lipman et al. | 623/20.27 |
| 2011/0125275 A1 * | 5/2011 | Lipman et al. | 623/20.11 |
| 2011/0125279 A1 * | 5/2011 | Lipman et al. | 623/20.27 |
| 2011/0125280 A1 * | 5/2011 | Otto et al. | 623/20.28 |
| 2011/0190897 A1 * | 8/2011 | Guidera et al. | 623/20.27 |
| 2012/0029649 A1 * | 2/2012 | Collazo et al. | 623/20.28 |
| 2012/0059483 A1 * | 3/2012 | Greenhalgh et al. | 623/20.11 |
| 2012/0095564 A1 * | 4/2012 | Mihalko et al. | 623/20.27 |

* cited by examiner

CONSTRAINED CONDYLAR KNEE DEVICE

CROSS REFERENCE TO RELATED APPLICATION

The present application claims the benefit of U.S. patent application Ser. No. 61/281,362, filed Nov. 16, 2009, which is hereby incorporated by reference in its entirety.

TECHNICAL FIELD

The present invention relates to prosthetic joints (e.g., orthopedic total knee arthroplasty (TKA) devices) and more particularly, to a constrained condylar knee (CCK) implant system for primary and revision surgery that offers improved stability of the joint during rotation (varus/valgus).

BACKGROUND

Joint replacement surgery is quite common and it enables many individuals to function normally when they otherwise would not be possible to do so. Typically, an artificial joint includes metallic, ceramic and/or plastic components that are fixed to existing bone. One of the more common joints that undergoes replacement surgery is the knee. Knee arthroplasty is a well known surgical procedure by which a diseased and/ or damaged natural knee joint is replaced with a prosthetic knee joint.

Artificial knee joints consist of essentially four components. The first component is a metallic tibia implant. The second component is a metallic femoral implant. The third component is a high-density polyethylene insert positioned between the two metal components. The fourth component, not part of the present invention, is a polyethylene patellar component. Together they form a joint that can provide a total replacement for a diseased native knee joint.

Traditionally the joint surfaces associated with the implant components are approximated by toroidal or donut shaped surfaces on both the insert and the condylar surfaces of the femoral component which transfer load from the femur to the tibia through the polyethylene insert. The total joint, once implanted, is stabilized and controlled in part by these surfaces and in part by the soft tissues surrounding and encapsulating the knee.

TKA devices can fail for reasons such as aseptic loosening, instability, or infection. Failure usually requires revision surgery. Revision implants have been developed that include a post on the polyethylene tibial component that articulates within a recess (intercondylar box) in the femoral component. The objective of this so called constrained condylar knee (CCK) implant is to rely on contact between the box and the post within the joint itself to restrain and limit rotation of the knee (varus/valgus rotations). This constraint is also beneficial in primary TKA if the soft tissues cannot be balanced to achieve an adequately stabilized and controlled joint.

SUMMARY

In contrast to conventional constrained condylar knee implants, the knee implants of the present invention includes nontoroidal surface geometry on the joint bearing surfaces to provide improved stability and performance of the joint during rotation (varus/valgus).

Additional features of the device tend to reduce contact stress on the post improving longevity and functionality of the joint.

There are several implementations of the improved geometry disclosed, but in general each condylar surface has at least two distinct radii in the coronal plane. During varus or valgus rotation, the point of contact between the femoral component and the tibial component moves laterally (outwardly). This point of contact migration alters the moment arm associated with soft tissue so that a much larger restoring moment is generated by muscles and ligaments, increasing the stability of the joint. The magnitude of this effect depends on the rotational angle of the joint. Additionally contact between a constraint post of the insert component (tibial) and an intercondylar box of the femoral component occurs gradually as a function of varus/valgus rotation and flexion-extension rotation (in a manner that reduces stress and wear on the post).

In one embodiment of the present invention, a knee joint prosthesis includes a femoral component having a first condylar bearing surface and a second condylar bearing surface. Each of the first and second condylar bearing surfaces has a cross-section in a coronal plane that exhibits at least two different radii. The prosthesis also includes a tibial component and an insert component associated with the tibial component. The insert component has bearing surfaces that are complementary to the first and second condylar bearing surfaces, wherein a contact point is established between the bearing surfaces of the insert component and the first and second condylar bearing surface. In accordance with the present invention and as a result of the above construction, varus and valgus rotation of the femoral component relative to the insert component causes the contact point to move laterally/outwardly as the knee is rotated. By shifting the contact pointy laterally (outwardly), the knee stability (i.e., stiffness) gradually increased.

In one embodiment, a femoral component for use in a knee joint prosthesis includes a body having a pair of laterally spaced condylar portions. A cross-section of each of the condylar portions is defined by at least two radii in a coronal plane, wherein a medial radius of each condylar portion is less than a lateral radius of the respective condylar portion.

Similarly, in one embodiment, a tibial component for a knee joint prosthesis includes a platform having an upper surface that includes first and second laterally spaced concavities. Each concavity is adapted for receiving one condylar portion of the femoral component and the tibial component includes a constraint post for reception in an intercondylar recess of the femoral component. Each of the first and second laterally spaced concavities includes a bearing surface that is defined by at least two different radii in a coronal plane.

Based on the foregoing, the present invention also includes a method for providing increasing stability in a knee joint prosthesis that includes a femoral component and a tibial component comprising the step of: moving in a lateral direction a point of contact between a condylar bearing surface of the femoral component and a complementary bearing surface of the tibial component as the knee undergoes varus or valgus rotation.

These and other aspects, features and advantages shall be apparent from the accompanying Drawings and description of certain embodiments of the invention.

BRIEF DESCRIPTION OF THE DRAWINGS

A few exemplary embodiments of the invention are depicted in the following figures, in which.

DETAILED DESCRIPTION OF EXEMPLARY EMBODIMENTS

Figure 1:
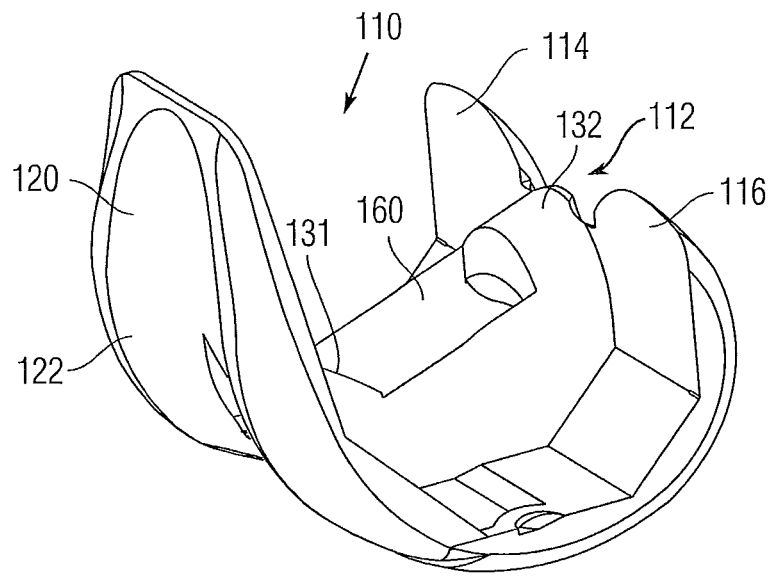
FIG. 1 is side perspective view of a femoral component that forms a part of a knee joint prosthesis.
Figure 2:
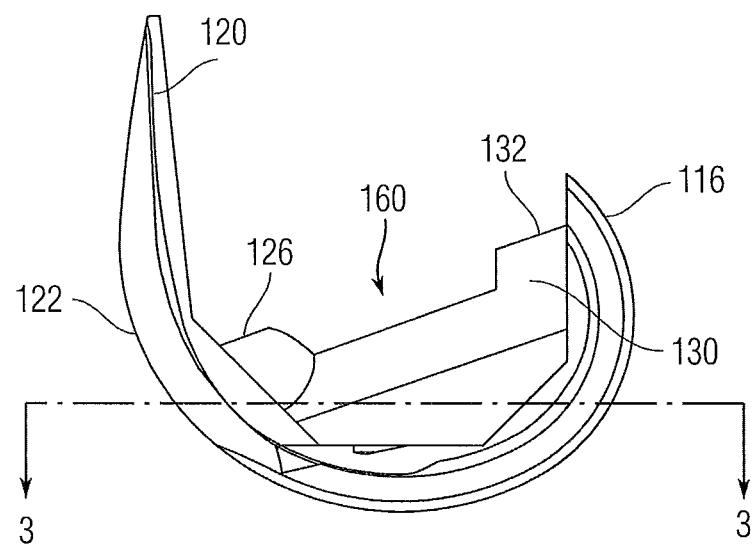
FIG. 2 is a side view of the femoral component of FIG. 1.

Failed primary TKA is not common but it is problematic for the patient. Revision knee arthroplasty is a significant percentage (~10%) of all TKA. TKA patients needing revision often have compromised collateral ligaments and subsequent varus/valgus instability. The common device used to treat these cases is a constrained condylar knee (CCK) implant. A CCK device includes a central post on the tibial insert that articulates with a recess in the femoral component (the intercondylar box). Contact between these structures limit rotation of the joint and prevent excessive varus/valgus rotation of the knee. The post has a relatively tight fit into the box of the femoral component allowing minimal rotation before contact. The post is in the center of the implant and made of a relatively soft material (ultra-high molecular weight polyethylene), so the post tends to fail via local deformation due to high contact stresses on the edges of the post, and thus the stability provided by the post is lost.

In conventional CCK devices, the varus/valgus stability is constant regardless of the flexion angle of the knee. However, a patient needs more stability in mid-flexion than at full extension. As a result, therein is a need to for an improved design where the implant device has variable varus/valgus stability matched to the functional requirements throughout the range of motion of the implant.

Current CCK implants primarily address varus/valgus stability. Motion analysis data during gait show that some patients experience anterior translation of the femur near full extension. Therefore, a CCK device that limits anterior translation is desirable and there is a need for such a device.

In view of the foregoing deficiencies associated with conventional CCK devices, the present invention is directed to an improved CCK device that overcomes the above noted deficiencies and provides improved stability over a range of different motions.

FIGS. 1-29 illustrate a joint prosthesis, in the form of a knee joint prosthesis 100, according to several exemplary embodiments of the present invention. The illustrated prosthesis 100 is of a constrained condylar knee (CCK) implant type.

The prosthesis 100 generally includes a femoral component 110 (FIGS. 1-4) for attachment to the femur and a tibial component 200 (FIGS. 9-13) for attachment to the tibia. The femoral component 110 is formed of a body 112 that has a pair of laterally spaced-apart femoral condylar portions 114, 116, each of which is smoothly convexly curved in a lateral profile generally to approximate the curvature of an anatomical femoral condylar and is convexly curved along its anteroposterior extent. The anterior parts of the condylar portions merge smoothly with convexly curved lateral portions 122 of a patellar portion 120. A midportion 126 of the patellar portion 120 intersects at its inferior extremity a superior wall or roof 132 of a box-like intercondylar portion 130 (stabilizer box), which together with the patellar portion 120, connects the condylar portions 114, 116.

As described in detail in commonly assigned U.S. patent application Ser. No. 11/860,423 (U.S. patent publication No. 2008/0097615) (which is hereby incorporated by reference in its entirety), the design of the intercondylar portion 130 has been modified so that the amount of bone that has to be removed is reduced.

The intercondylar portion 130 is defined by an arcuate shaped wall 131 that likewise defines the roof 132 of the portion 130. The roof 132 can thus be thought of as the apex region of the arcuate shaped wall 131. The illustrated arcuate shaped wall 131 has a semi-circular shape or "rounded shape" that is designed to be received within a complementary rounded bone notch or opening. The present intercondylar design thus does not include a well defined roof that is generally horizontal (parallel to a nominal base plane). Significantly less bone is removed in the design of the present invention since the hard squared edges of the conventional femoral box notch are absent in the rounded femoral box notch made according to the present invention. The cylindrical shape of the femoral box notch made in the femur can be cut with a rotating cutter, such as a drill or reamer, which eliminates the additional stress concentrations created by the overcut slots that are created when cutting the box geometry with a sagittal saw. In other words, the cylindrical box geometry can be cut without creating stress concentrations in the corners where a sagittal saw would extend the cut past the edge of the box.

An opening 160 is preferably formed in the roof 132 of the intercondylar portion 130 and in particular, the opening 160 is formed in the arcuate shaped wall 131. Since the roof in the prior art intercondylar portion is a flat, planar surface, the opening was contained in the same plane; however, the arcuate shape of the wall 131 causes the opening 160 to lie not in a single plane, but instead, the opening 160 lies in an arcuate shaped surface. The opening 160 allows for placement of an intramedullary nail in the event of a distal femoral fracture after total knee replacement.

An underside of the femoral component 110 includes a surface 170 (which can be an arcuate surface—e.g., a curved saddle shaped surface as described in the '615 publication). This surface 170 is located adjacent the opening 160 and faces the tibial component 200 when the two components 110, 200 are assembled. The arcuate surface 170 is proximate the patella portion 120. According to the present invention, this surface 170 is configured and dimensioned so as to mate with a complementary surface of the tibial component 200 when the components 110, 200 mate together as described below.

The femoral component 110 can include a cam follower surface (not shown) that is located adjacent the opening 160 at the posterior side of the femoral component 110. In particular, the cam follower surface is positioned between the condylar portions 114, 116 and is described in more detail in the '615 publication.

The femoral component 110 can be made of a number of different materials, including a surgical grade, durable metal, such as a 316L stainless steel or a chrome-cobalt-molybdenum meeting ASTM Standard #F75. All surfaces which are external to the bone are preferably highly polished.

Straight Box Femoral Component

Figure 3:
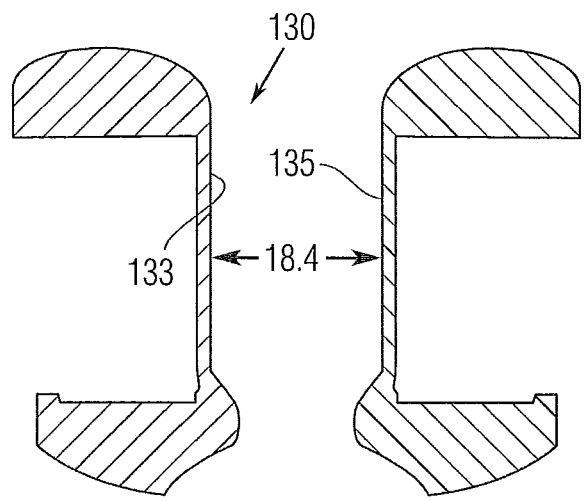
FIG. 3 is a cross-sectional view taken along the line 3-3 of FIG. 2.

FIGS. 1-4 show the femoral component 110 according to one embodiment. The femoral component 110 according to this embodiment can be referred to as having a straight box. The intercondylar portion 130 (stabilizer box) includes a first inner wall 133 and an opposite second inner wall 135 that terminate at the roof structure of the box. In this first embodiment, the two inner walls 133, 135 are parallel to one another as shown in FIG. 3. FIG. 3 thus shows the distance between the inner walls 133, 135 as being uniform along the length of the walls 133, 135.

Figure 4:
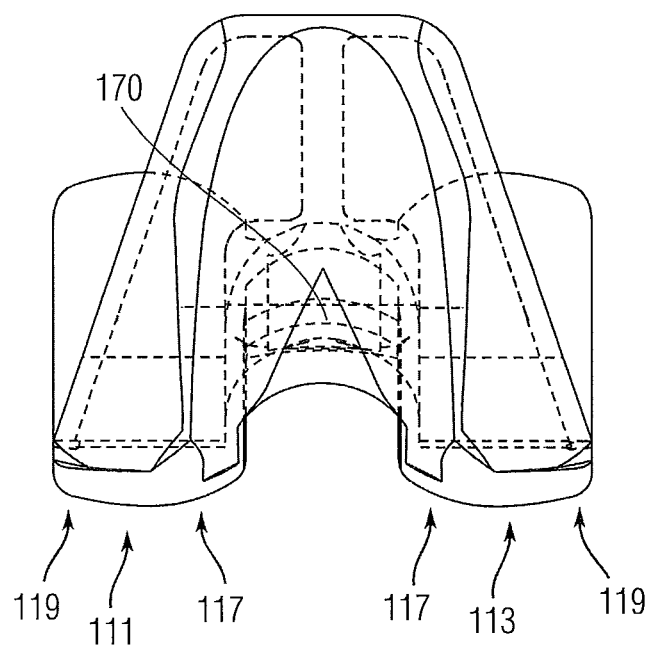
FIG. 4 is an end view of the femoral component of FIG. 1.

In yet another aspect of the present invention and as described herein, in the present invention, the shape of the femoral component 110 (as well as the tibial component 200) so that the geometry is no longer a swept circular shape (i.e., a toroid). Instead, the swept geometry consists of two tangent radii, for which the medial radius of the condyle is smaller than the lateral radius. More specifically, an underside of the femoral component 110 includes a first condylar bearing surface 111 and a second condylar bearing surface 113. FIG. 4 generally shows the medial radius 117 of each condylar bearing surface 111, 113 and the lateral radius 119 of each condylar bearing surface 111, 113, with the medial radius 117 being less than the lateral radius 119.

In yet another embodiment, each of the condylar bearing surfaces 111, 113 can be formed by a surface that is created with a multiple radius curve (spline) where the medial part of the curve has smaller radii than the lateral part. Thus, the surface can be defined by more than two radii.

Stepped Box Femoral Component

Figure 5:
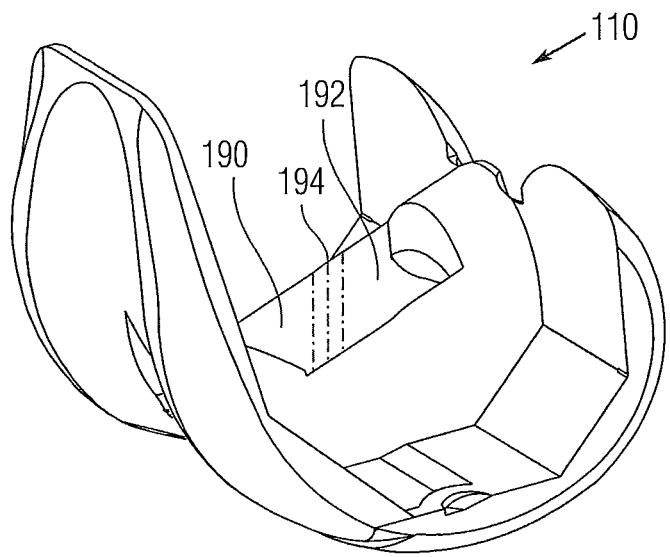
FIG. 5 is a side perspective view of a femoral component, according to a second embodiment.
Figure 6:
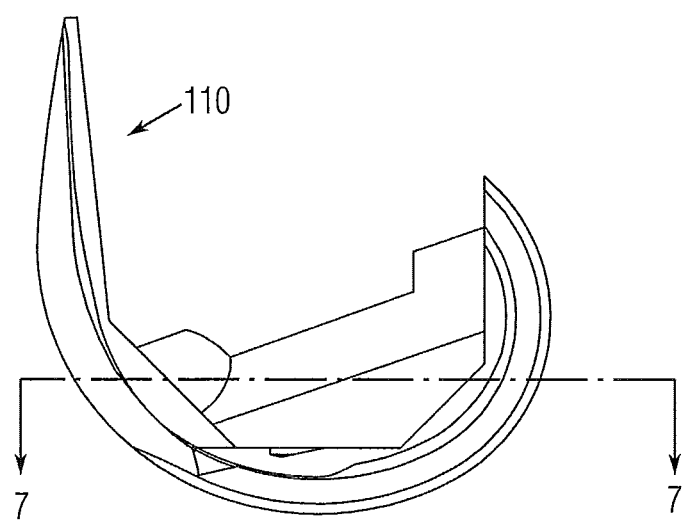
FIG. 6 is a side view of the femoral component of FIG. 5.

FIGS. 5-8 illustrate a femoral component 110 according to another embodiment. The femoral component 110 of FIGS. 5-8 is very similar to the femoral component 110 of FIGS. 1-4 in that it includes first and second condylar bearing surfaces 111, 113 that each is formed and defined by at least two tangent radii. The different between the femoral component 110 of FIGS. 5-8 and the femoral component 110 of FIG. 1-4 is that the first inner wall 133 and an opposite second inner wall 135 are not parallel walls but instead, the walls 133, 135 at least have one section that has a non-parallel orientation. As shown in FIG. 5, each of the walls 133, 135 includes a first section 190 (anterior portion) at one end of the wall 133, 135 and a second section 192 (posterior portion) at the opposite end of the wall 133, 135, with a third section 194 being a transition portion that is located between the first section 190 and the second section 192. The distance between the opposite walls 133, 135 varies depending upon the location along the length of the walls 133, 135.

Figure 7:
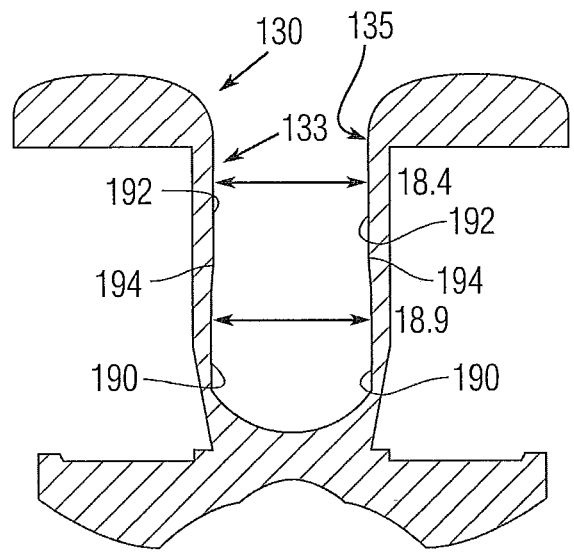
FIG. 7 is a cross-sectional view taken along the line 7-7 of FIG. 6.
Figure 8:
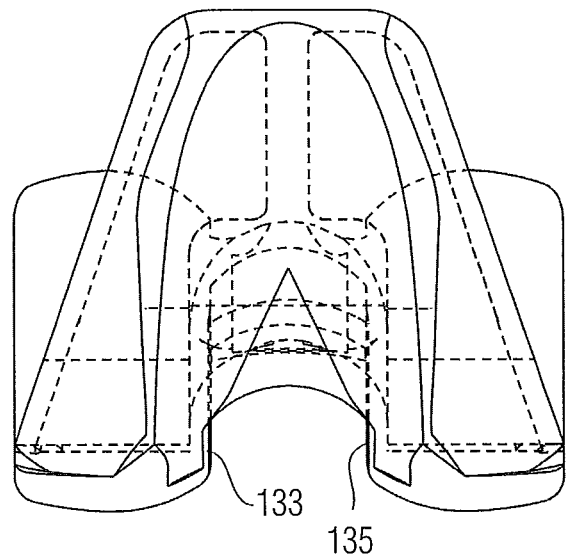
FIG. 8 is an end view of the femoral component of FIG. 5.
Figure 9:
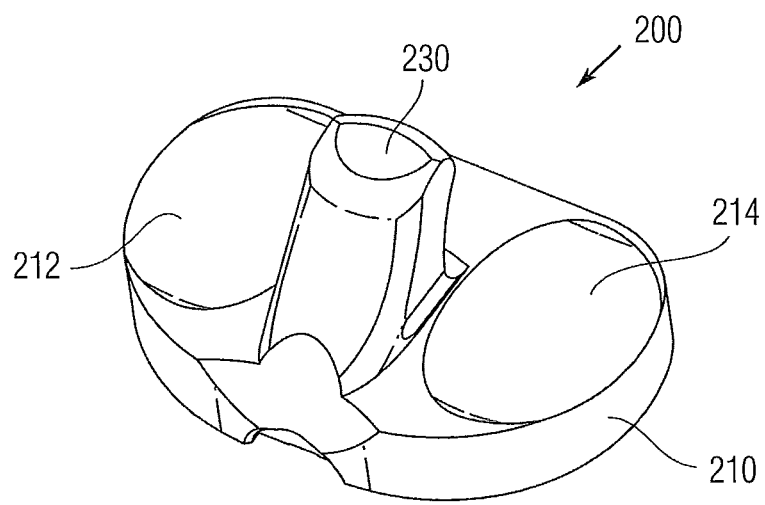
FIG. 9 is an end and side perspective view of a tibial component that forms a part of a knee joint prosthesis.
Figure 10:
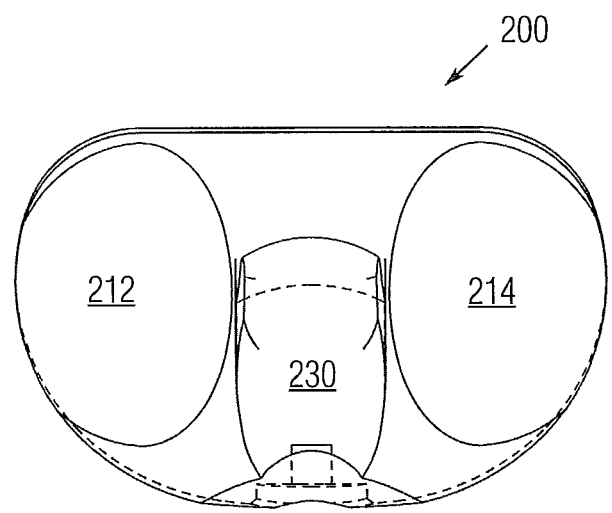
FIG. 10 is a top plan view of the tibial component of FIG. 9.
Figure 11:
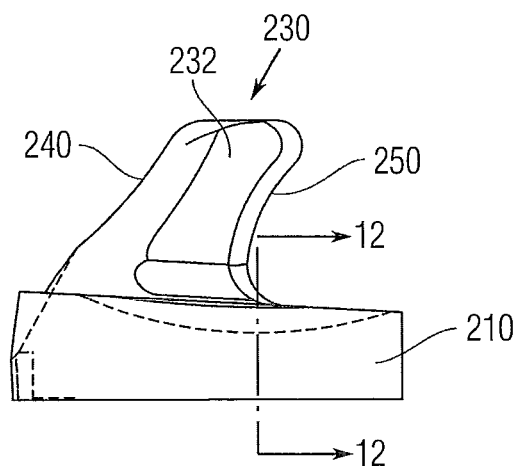
FIG. 11 is a side elevation view of the tibial component of FIG. 9.

In one embodiment as shown in FIG. 7, the walls 133, 135 have a stepped construction in that the first sections 190 are parallel to one another and similarly, the second sections 192 are parallel to one another; however, the distance between the first sections 190 is different than the distance between the second sections 192. The third section 194 is a region that is not-parallel to the other third section 194 and instead is a region where the wall has a sloped surface.

In the illustrated embodiment, the anterior portion of the box is wider than the posterior portion and accordingly, the distance between the first sections 190 is greater than the second sections 192 as shown in FIG. 7.

Figure 29:
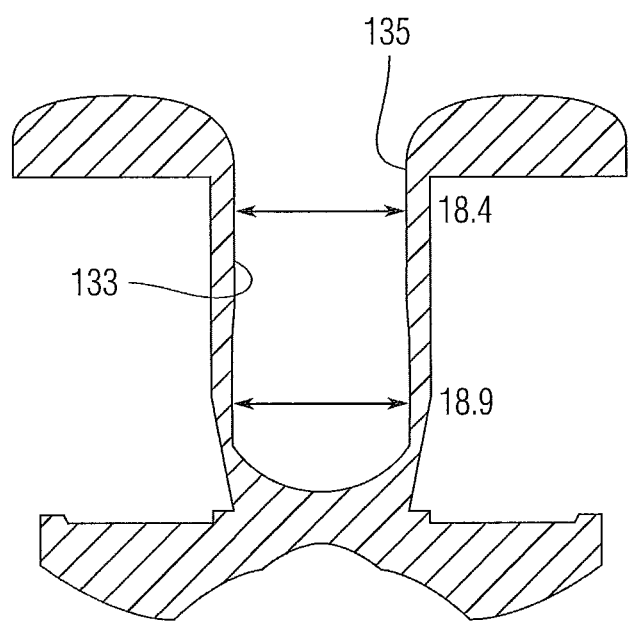
FIG. 29 is a cross-sectional view of the femoral component showing a tapered box construction.

In another embodiment shown in FIG. 29, the walls 133, 135 can have a tapered construction in that the walls 133, 135 are not parallel but instead are oriented in a converging orientation. The walls 133, 135 can each have a smooth appearance with the distance between the walls 133, 135 becoming progressively greater in the anterior direction. Thus, as in the previous embodiment, the anterior portion represents the widest portion of the box.

Tibial Component

Now referring to FIGS. 9-12, the prosthesis 100 includes tibial component 200. The tibial component 200 is part of a tibial assembly that includes a tibial platform or tray (not shown) from which a tibial stem extends downwardly and is constructed for insertion and attachment to the tibia. An upper surface of the tibial tray is constructed to receive and attach to a bearing component 200 (tibial insert) that is positionable between the femoral component 110 and the tibial tray. As described in greater detail below, the tibial insert 220 cooperates with the femoral component 110 to provide for the desired kinematics of the knee prosthesis.

As shown in the figures, the tibial component 200 includes an oblong, rounded, disc-like plateau portion 210 that has an upper surface that can be flat or have some other predetermined contour. A pair of laterally spaced-apart, oblong concavities 212, 214 is formed along the upper surface for receiving femoral condylar portions 114, 116 of the femoral component 110 as described below. The "nested" support of the femoral component 110 stabilizes the prosthetic joint, but still permits antero-posterior translation, lateral angulation and rotation, all of which are involved in normal function of the anatomical knee joint.

The tibial insert 220 also preferably includes a base-like fixation portion that extends from a bottom surface of the plateau portion 210 to allow the tibial insert 220 to be attached to the tibial tray using conventional techniques and methods.

The tibial insert 220 also includes a stabilizing post 230 that extends upward from the plateau portion 210 between the concavities 212, 214 and is positioned to be received in an intercondylar recess of the femoral component 110. The stabilizing post 230 is generally triangular in a lateral profile and is defined by side surfaces 232, an anterior face 240, and an opposite posterior face 250. The side surfaces 232 of the stabilizing post 230 are in sufficient clearance from the lateral walls of the femoral intercondylar recess to allow for normal lateral angulation and rotation when assembled with the femoral component 110 of the prosthetic knee joint. Exemplary constructions of the posterior face 250 and anterior face 240 of the stabilizing post 230 are described in the '615 publication.

Figure 12:
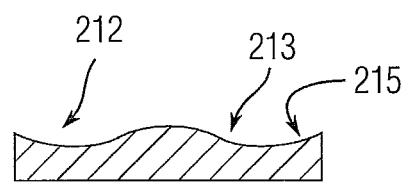
FIG. 12 is a cross-sectional view taken along the line 12-12 of FIG. 11.

As mentioned above, the pair of laterally spaced-apart, oblong concavities 212, 214 is formed along the upper surface for receiving femoral condylar portions 114, 116 of the femoral component 110 and therefore, have complementary shapes relative to the condylar portions 114, 116. Accordingly and similar to the femoral component 110, the contact bearing surfaces 212, 214 of the tibial component 200 do not have swept circular shape (i.e., a toroid) but instead, the swept geometry consists of at least two tangent radii (curved articular geometry). FIG. 12 illustrates the swept geometry of each of the bearing surfaces 212, 214 and in particular and in accordance with the illustrated embodiment, each bearing surface 212, 214 has a first radius (medial) 213 and a second radius (lateral) 215, with the medial radius 213 being less than the lateral radius 215. This design is complementary to the design of the bearing surfaces of the femoral component 110 and therefore, when the two mate together, the reduced medial radii portions of the component overlie one another and lateral radii portions of the components overlie one another.

In one embodiment, the ratio femoral to tibial radii is approximately 0.85 to 0.95.

Tapered Stabilizing Post

Figure 13:
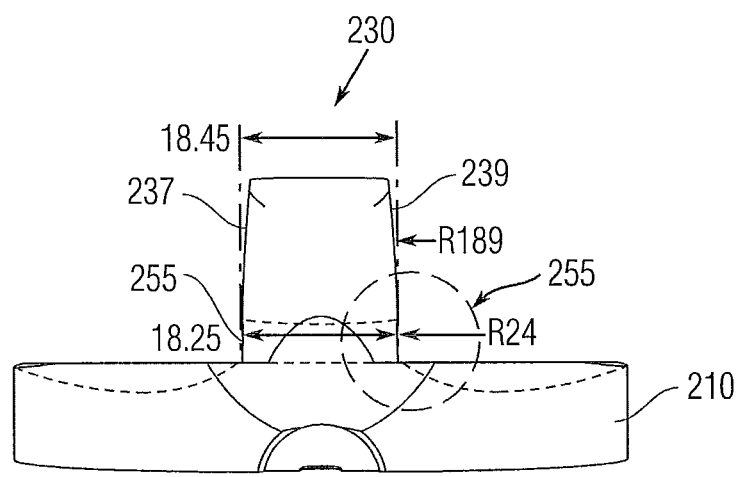
FIG. 13 is an end view of the tibial component.

With reference to FIG. 13, the geometry of the tibial post has been modified from current designs to reduce local deformation of the tibial post 230. Conventional tibial posts have flat medial and lateral faces. In contrast, the post 230 of a tibial component according to one embodiment of the present invention has been replaced by faces that are slightly curved. Opposing first and second (medial and lateral) faces 237, 239, respectively, of the post 230 are not flat (parallel to one another) but instead, the faces 237, 239 are curved. As shown in FIG. 13, in a direction toward the top of the post 230, the opposing faces 237, 239 diverge from being parallel to one another and are inwardly tapered toward one another.

In the illustrated embodiment, the faces 237, 239 have a radius of about 189 mm; however, it will be appreciated that this value is merely exemplary in nature and the faces can be formed to have a curvature defined by a radius having a different value.

As a result of the curved nature of the post 230 and as the femoral component 110 rotates, contact with the post 230 occurs over a broader surface than if the post 230 were flat as in the case of conventional posts.

Figure 20:
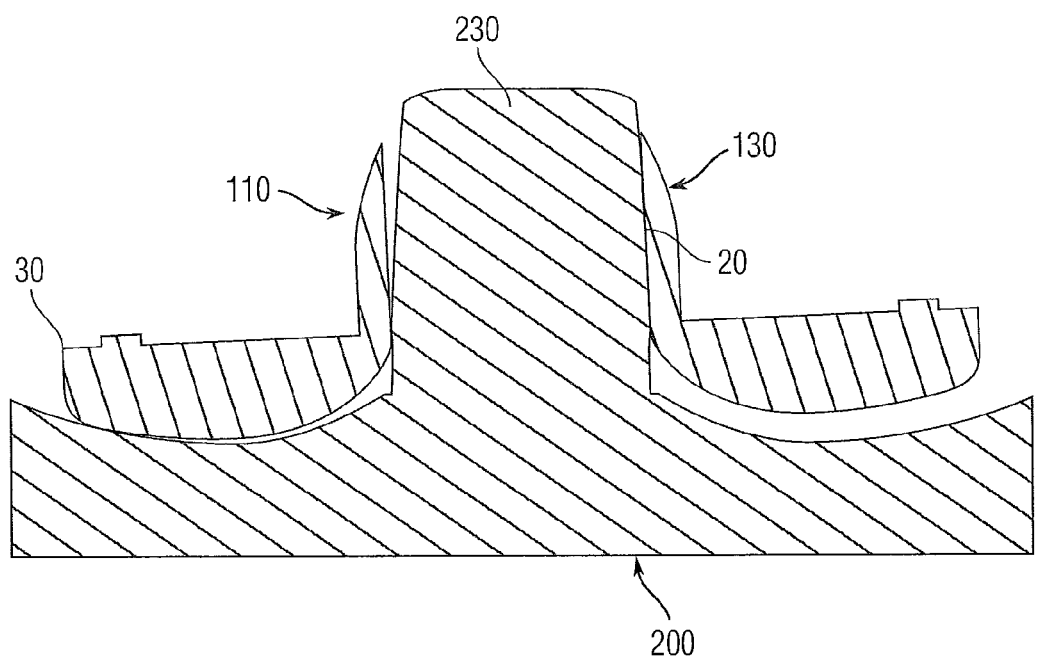
FIG. 20 is a cross-sectional view taken along the line 20-20 of FIG. 18.

Also, as shown in FIG. 13, a slight recess 255 has been built into the tibial post 230 at a lower portion thereof to reduce contact between the inside edge of the femoral component 110 and the tibial post 230. In effect, the recess 255 can be a slightly shaved region of the post 230. This "relief" feature is shown in FIG. 20. In addition, the contact of the post against the intercondylar box prevents the femoral component from sliding back medially, therefore maintaining the improved varus/valgus stability when the knee is rotated in the coronal plane.

Figure 30:
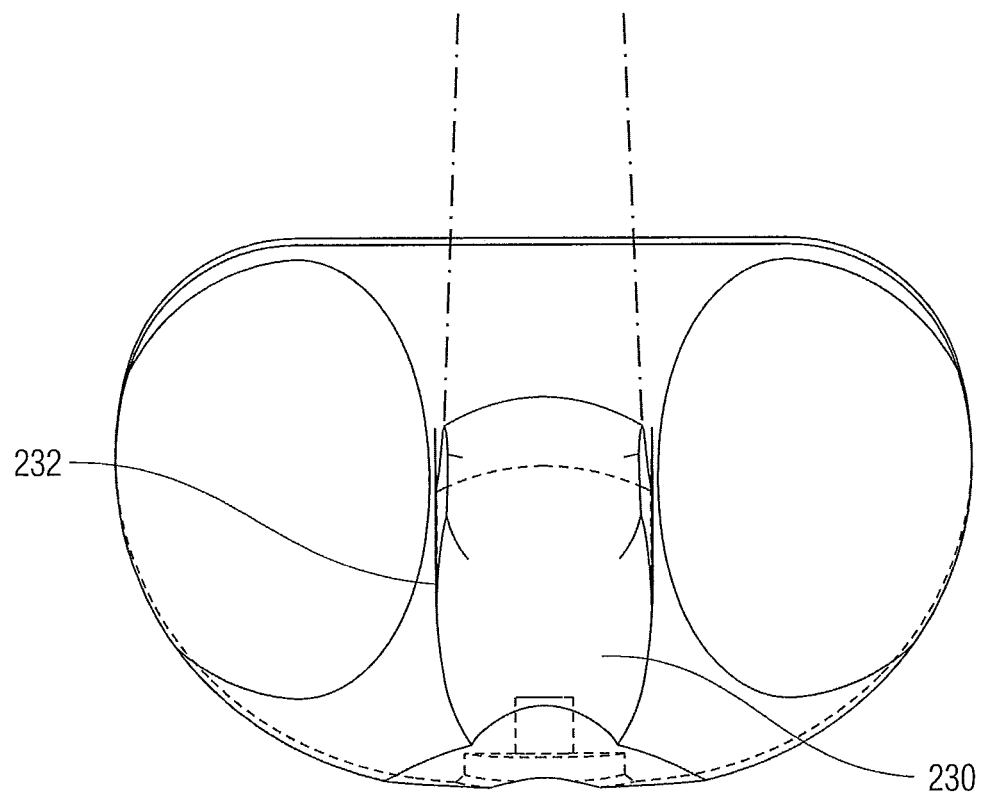
FIG. 30 is a top plan view of a tibial insert showing a tapered stabilizing post according to another embodiment.

As mentioned above, in one embodiment (FIG. 29), the walls 133, 135 of the intercondylar box have a tapered construction (the anterior portion represents the widest portion of the box) and similarly, as shown in FIG. 30, the walls 232 of the post 230 can have a complementary design to mate with the tapered walls 133, 135. More specifically, the post 230 has a complementary tapered shape as shown in the figure. This permits proper and complementary reception of the post within the box and engagement of the respective tapered surfaces.

Improved Varus/Valgus and Anterior-Posterior Stability

As described herein, the prosthesis 100 according to the present invention consists of a modified femoral component 110 of either a straight box configuration (FIGS. 1-4) or a stepped or tapered box configuration (FIGS. 5-8) and a complementary, mating tibial component (tibial insert) 200. The present design improves the stability of the prosthesis 100 (CCK device) by using the condylar articulation of the knee implant 100 acting in concert with the central post 230 to provide both varus/valgus and anterior-posterior stability.

A primary stabilizer of the knee to varus/valgus rotation is the ability of the knee to transfer more load from one condyle to the other and, under more extreme loads, to lift off and load a single condyle when rotated in the coronal plane. This stabilization occurs with the natural knee as well as any bicondylar knee implant. However, in a typical bicondylar implant, where the femoral component has toroidal geometry, the contact point between the femoral component and tibial component tends to stay at the center of the condyle, especially when the joint is under compressive axial load.

Figure 14A:
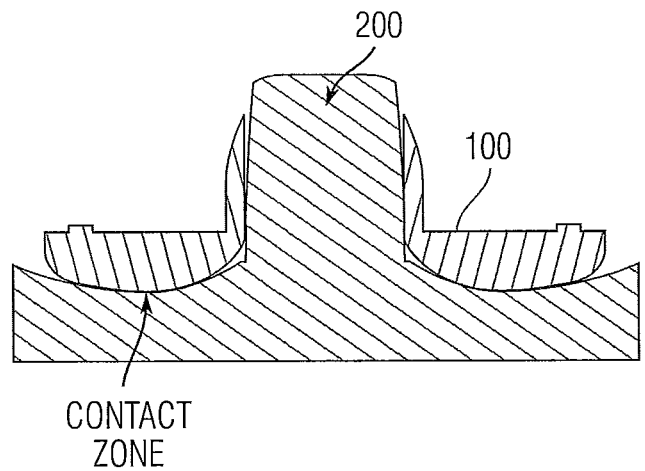
FIGS. 14A and 14B are cross-sectional views of the femoral component mated with the tibial component in different orientations showing migration of a bearing contact point between the two components when the knee joint prosthesis has undergone varus/valgus rotation.
Figure 14B:
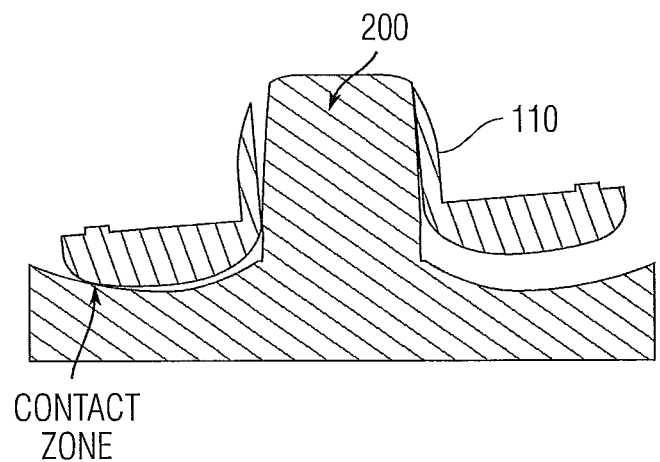

In accordance with the present invention, the modified shape of the femoral component 110 and tibial component 200 so that the geometry is no longer a swept circular shape (i.e., a toroid). Instead, the swept geometry consists of the two tangent radii described above, for which the medial radius of the condyle is smaller than the lateral radius. It will therefore be appreciated that both the femoral component 110 and the tibial component 200 have this complementary geometry. As the knee rotates into varus or valgus, the contact point between the two components 110, 200 shifts away from the center of the knee, and thus the restoring moment generated by contraction of the quadriceps and/or hamstring muscles increases. FIGS. 14A and 14B show the shifting nature of the contact point. In FIG. 14A, the contact point between the femoral component 110 and the tibial component 200 is indicated by the arrow. FIG. 14B shows that when the knee undergoes varus/valgus rotation, the contact point (as indicated by the arrow) between the femoral component 110 and the tibial component 200 shifts and more specifically, shifts in a direction away from the center. In other words, the design of the femoral component 110 and the tibial component 200 provide for a translating bearing contact point (in the lateral/outward direction) between the femoral component 110 and the tibial component 200 as the knee undergoes varus or valgus rotation.

Figure 15:
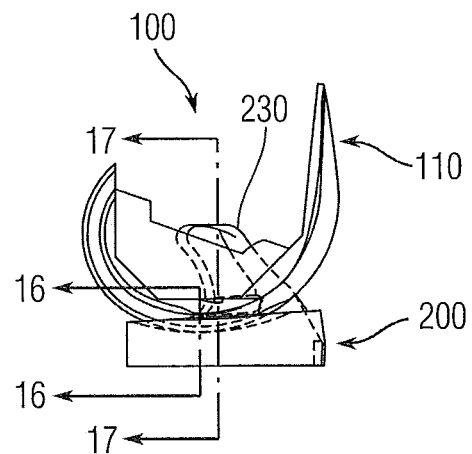
FIG. 15 is a side elevation view showing the conformation of the femoral component of FIG. 1 with the tibial component at 0 degrees rotation and full extension (0 degrees flexion)
Figure 16:
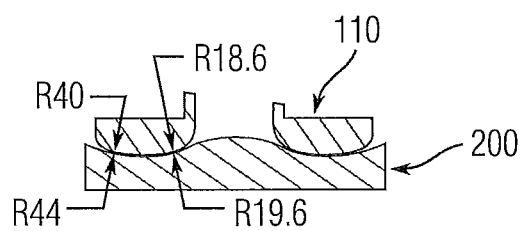
FIG. 16 is a cross-sectional view taken along the line 16-16 of FIG. 15.
Figure 17:
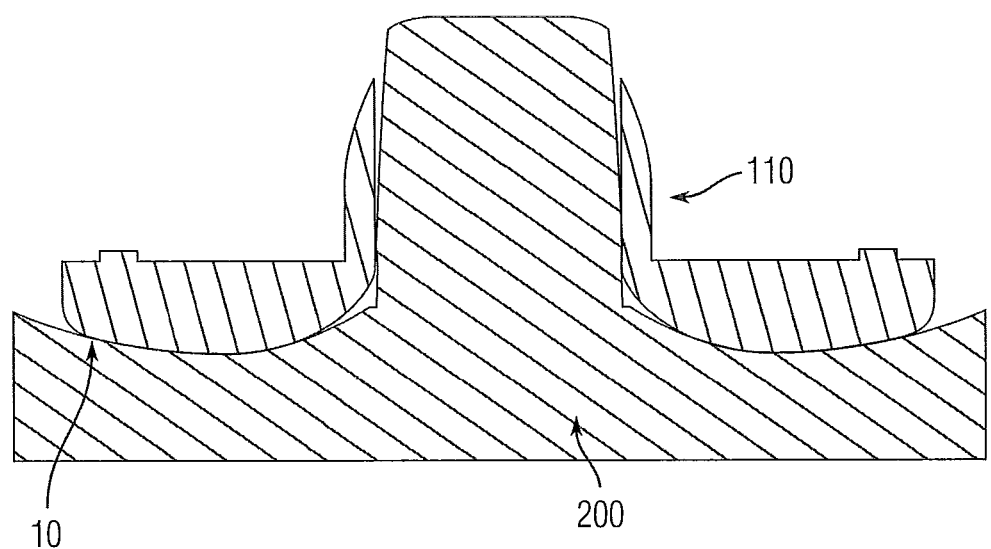
FIG. 17 is a cross-sectional view taken along the line 17-17 of FIG. 15.

FIGS. 15-17 illustrate the conformation of the femoral component 110 (straight box embodiment of FIGS. 1-4) with the tibial component 200 at 0 degrees rotation and full extension (flexion). In FIG. 16, the multi radii construction of the femoral component 110 and the tibial component 200 is shown.

In addition, as shown in FIG. 17, there is a slight clearance that exists between the lateral condylar portion of the femoral component 110 and the lateral tibial component 200 when the knee is in 0° of rotation. The clearance is indicated at reference character 10.

Based on the geometry of a standard size knee, the contact point can be lateralized by approximately 15 mm. However, it will be appreciated that this value is merely exemplary in nature and other values are equally possible depending upon the construction of the device. Shifting the contact force location laterally can increase the restoring moment of the knee by approximately 70%.

Figure 18:
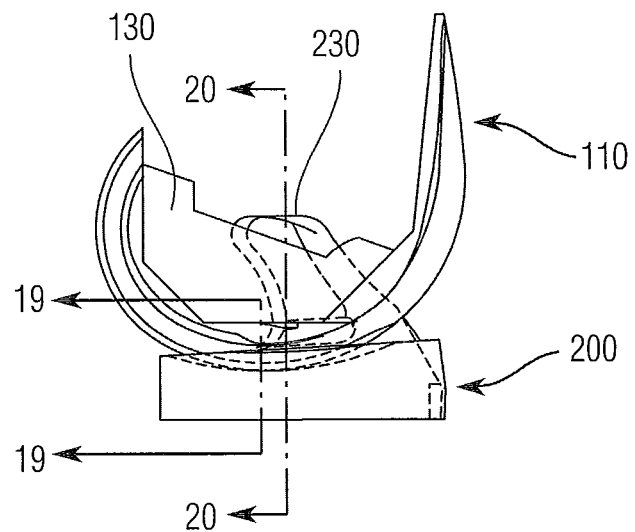
FIG. 18 is a side elevation view showing the conformation of the femoral component (FIG. 1) with the tibial component at 2 degrees rotation and full extension (0 degrees flexion)
Figure 19:
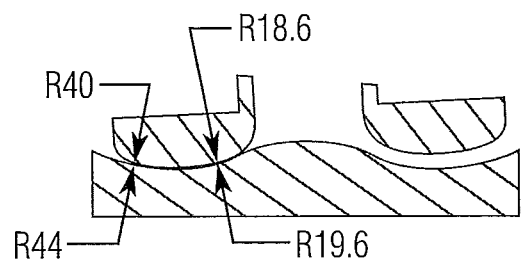
FIG. 19 is a cross-sectional view taken along the line 19-19 of FIG. 18.

FIGS. 18-20 illustrate the conformation of the femoral component 110 (straight box configuration of FIGS. 1-4) with the tibial component 200 at 2 degrees rotation and full extension. It will be appreciated that at about 2° of rotation, the post 230 contacts the box 130 of the femoral component 110, and the post/box articulation provides additional constraint to varus/valgus rotation as shown in FIG. 20. In FIG. 19, the multi radii construction of the femoral component 110 and the tibial component 200 is shown and indicated by the reference characters. In FIG. 20, the point of contact between the post 230 and the box 130 is shown at reference character 20, while contact between the condylar portion of the femoral component 110 and the tibial component 200 is indicated at reference character 30.

By shifting the contact point laterally (see FIGS. 14A and 14B), the knee stability (i.e., stiffness) gradually increases. Then, as the curved post 230 accepts more of the load, the varus/valgus stiffness of the knee further increases. This gradual increase in stiffness is in contrast to conventional CCK implants where once the knee lifts off, the stiffness remains relatively constant. The shifting bearing contact point provides a CCK implant design that overcomes the deficiencies of the conventional CCK implants.

While there are existing knee systems that have articular geometry that is not toroidal, these systems employ a nearly flat on flat configuration in the coronal plane. These designs will lateralize the contact point upon varus/valgus loading. The difference between these conventional designs and the present design is that with the curved articular geometry of the present prosthesis 100, the contact point shifts laterally in a gradual manner. In this way, the stiffness of the knee increases gradually, rather than increasing in a step-wise fashion after liftoff. In addition, a design that immediately lateralizes the contact point, as in the conventional devices, is at a greater risk for extreme edge loading of the tibial insert, putting the polyethylene implant, the fixation to the underlying bone, and the bone itself at risk.

Varus/Valgus Stability in Mid-Flexion

As described herein, in the embodiment shown in FIGS. 5-8, the femoral component 110 can be modified to have a step-off on the surfaces 131, 133 of the box of the femoral component 110. When the femur is in extension rotated into varus/valgus, the contact between the post and the femoral component 110 occurs at the wider, anterior portion of the box.

Figure 21:
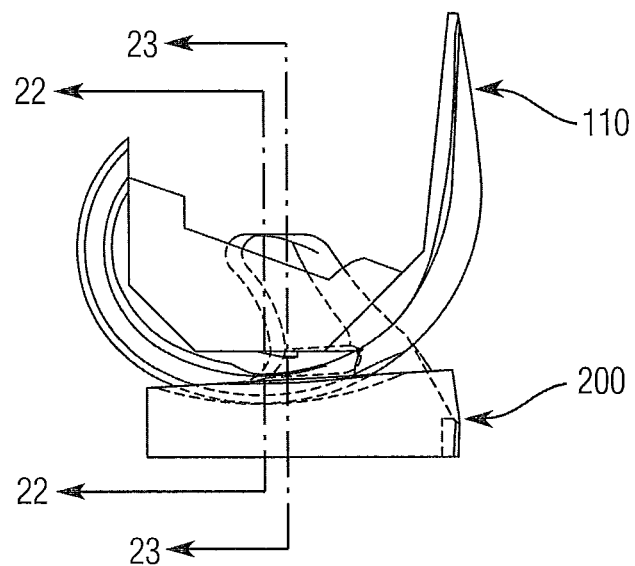
FIG. 21 is a side elevation view showing the conformation of the femoral component (FIG. 5) with the tibial component at 5 degrees rotation and full extension (flexion)
Figure 22:
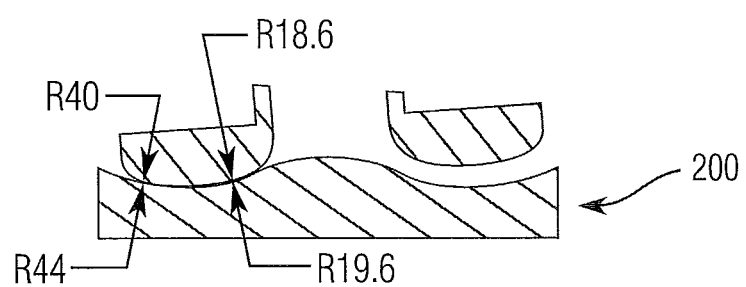
FIG. 22 is a cross-sectional view taken along the line 21-21 of FIG. 20.
Figure 23:
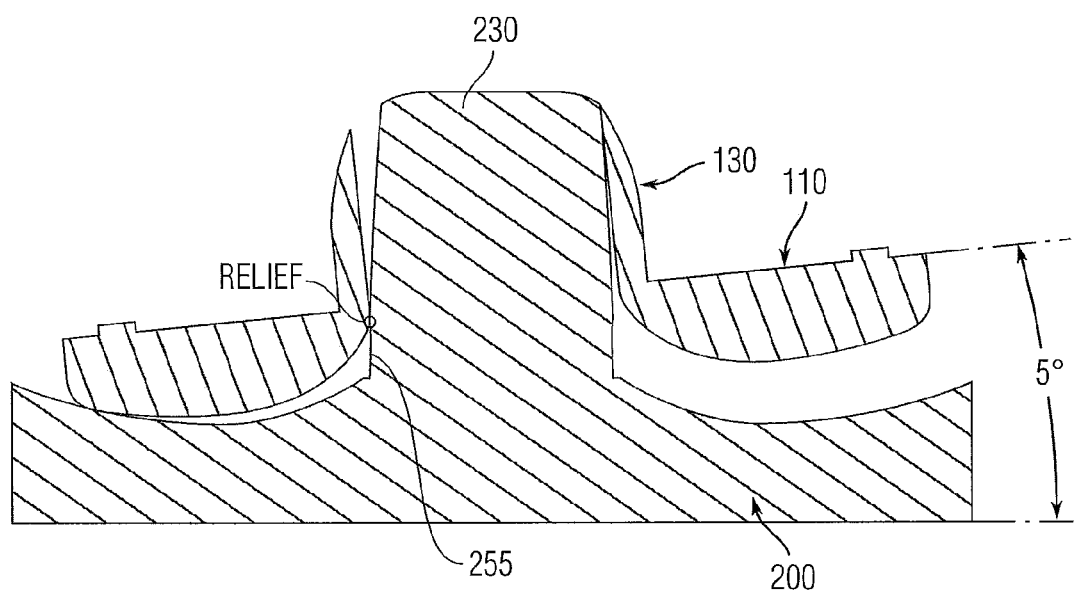
FIG. 23 is a cross-sectional view taken along the line 22-22 of FIG. 20.
Figure 24:
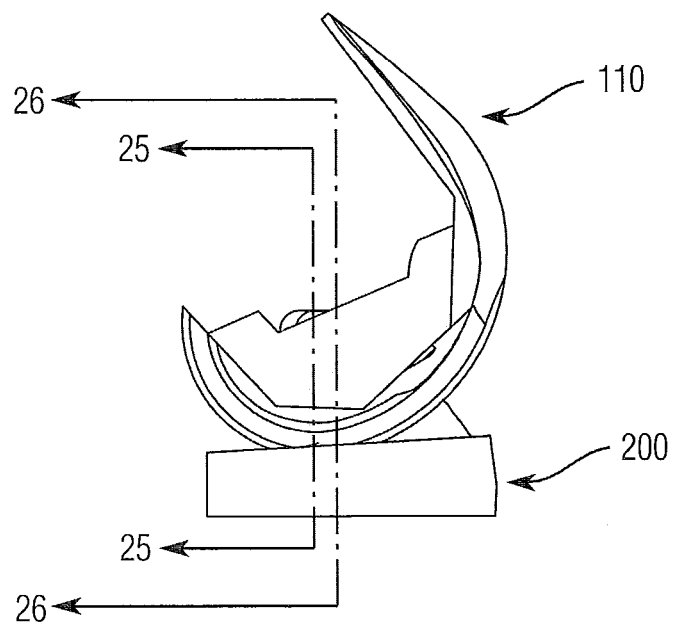
FIG. 24 is a side elevation view showing the conformation of the femoral component (FIG. 5) with the tibial component at 2 degrees rotation and 45 degrees flexion.
Figure 25:
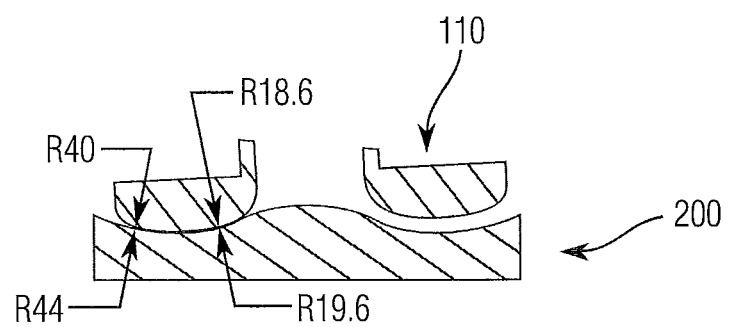
FIG. 25 is a cross-sectional view taken along the line 25-25 of FIG. 24.
Figure 26:
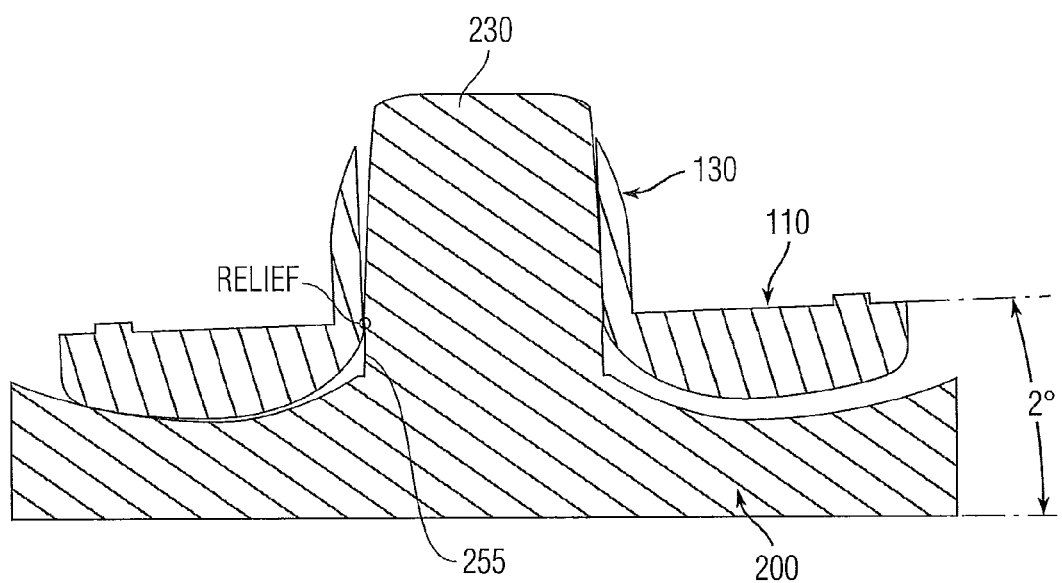
FIG. 26 is a cross-sectional view taken along the line 26-26 of FIG. 24.

FIGS. 21-23 show the conformation of the femoral component 110 (stepped box design of FIGS. 5-8) with the tibial component 200 at 5 degrees rotation and full extension, thereby causing the contact point to move laterally. In FIG. 22, the multi radii construction of the femoral component 110 and the tibial component 200 is shown and indicated by the reference characters. FIGS. 24-26 show the conformation of the femoral component 110 (stepped box design of FIGS. 5-8) with the tibial component 200 at 2 degrees rotation and full extension.

The wider box configuration, due to the stepped wall or tapered wall construction, permits greater rotation until contact is made between the post 230 and the box 130 (in this embodiment, approximately 5° of rotation as shown in FIG. 23). Relief provided by recessed section 255 is also shown in FIG. 23. As shown in FIGS. 24-26, when the femur is in the mid-flexion position (about 45° of flexion) and rotated into varus/valgus, the contact between the post 230 and the femoral component 110 occurs at the posterior, narrower portion of the box 130 as best shown in FIG. 26. At this location, only 2° of rotation can occur before contact between the post 230 and the box 130.

Figure 27:
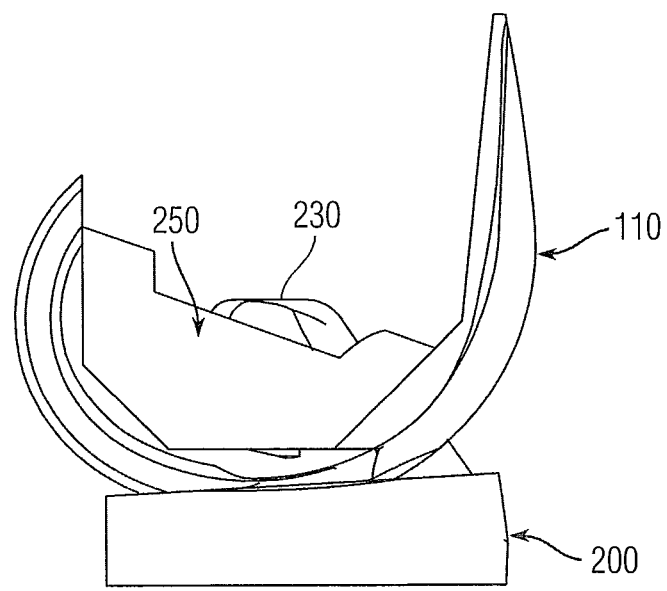
FIG. 27 is a side elevation view showing the conformation of the femoral component (FIG. 5) with the tibial component at zero degrees flexion.
Figure 28:
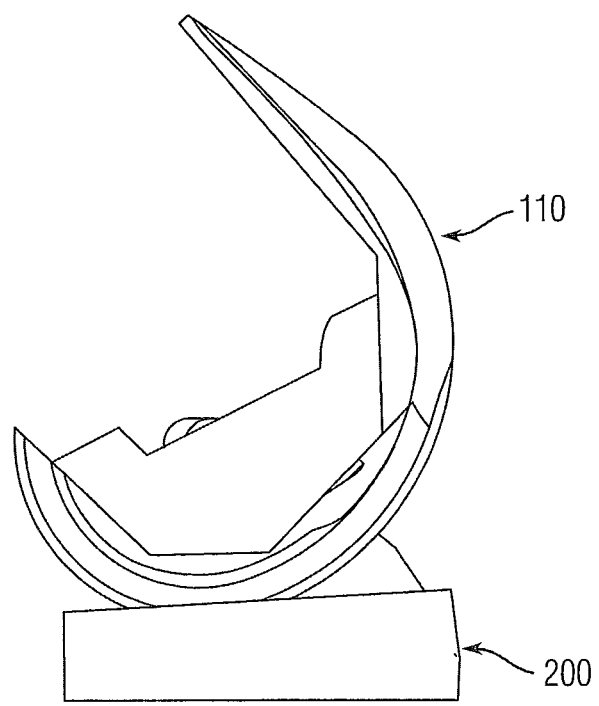
FIG. 28 is a side elevation view showing the conformation of the femoral component (FIG. 5) with the tibial component at 45 degrees flexion.

To reduce the amount of anterior translation of the knee at near full extension, the proximal posterior surface, as indicated at 250, of the post 230 has been extended posteriorly as shown in FIGS. 27 and 28. The additional posterior material reduces anterior translation by approximately 5 mm. The extension of material is only included on the upper portion of the post 230 so the kinematics of the post/cam articulation is not affected during flexion.

It will be appreciated that the present invention is suitable for revision knee replacement or primary knee replacement for patients with poor collateral ligaments (e.g., extreme valgus deformity). The improved designs of the bearing surfaces of the implant components provide improved stability and performance of the joint during rotation (varus/valgus). The modified surface geometry of the present components provides a better match to patient anatomic requirements through a full range of motion (flexion-extension and rotations).

It will be appreciated that any numerals set forth in the drawings represent exemplary dimensions and only unless otherwise mentioned, in the metric unit of millimeters.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A knee joint prosthesis comprising:
a femoral component having a first condylar bearing surface and a second condylar bearing surface, wherein each of the first and second condylar bearing surfaces has a convex shape and has a cross-section in a coronal plane that exhibits at least two different radii that define the convex shape of the bearing surface;
a tibial component; and
an insert component associated with the tibial component and having bearing surfaces that are complementary to the first and second condylar bearing surfaces, wherein a contact point is established between the bearing surfaces of the insert component and the first and second condylar bearing surfaces;
wherein varus and valgus rotation of the femoral component relative to the insert component causes the contact point to move laterally when the tibial component is in near full extension relative to the femoral component.

2. The knee joint prosthesis of claim 1, wherein a medial radius of each of the first and second condylar bearing surfaces is less than a lateral radius thereof, the medial radius and lateral radius being two tangent radii.

3. The knee joint prosthesis of claim 1, wherein the insert component includes first and second laterally spaced-apart, oblong concavities formed along an upper surface for receiving the first and second condylar bearing surfaces of the femoral component to provide a nested configuration between the femoral component and the insert component, the oblong concavities defining the bearing surfaces of the insert component.

4. The knee joint prosthesis of claim 3, wherein each bearing surface of the insert component includes a lateral portion and a medial portion, with a radius of the medial portion being less than a radius of the lateral portion.

5. The knee joint prosthesis of claim 1, wherein the femoral component includes an intercondylar box and the insert component includes a constraint post for reception within the intercondylar box.

6. The knee joint prosthesis of claim 5, wherein the constraint post has a medial face and a lateral face, each of the medial and lateral faces having a curved shape.

7. The knee joint prosthesis of claim 6, wherein the constraint post further includes a recessed section formed along a lower portion thereof to reduce contact between an inside edge of the femoral component and the constraint post.

8. The knee joint prosthesis of claim 5, wherein the intercondylar box includes a first inner wall and an opposing second inner wall, each of the first and second inner walls having a stepped construction in that an anterior portion of the intercondylar box is wider relative to a posterior portion of the intercondylar box as measured between the first and second inner walls.

9. The knee joint prosthesis of claim 8, wherein the knee is in extension and rotated in a varus or valgus direction, contact between the constraint post and the femoral component occurs at the wider anterior portion of the intercondylar box.

10. The knee joint prosthesis of claim 5, wherein the intercondylar box includes a first inner wall and an opposing second inner wall that are inwardly tapered relative to one another in a direction toward a posterior portion of the intercondylar box.

11. The knee joint prosthesis of claim 1, wherein a clearance exists between the lateral condylar bearing surface and a lateral bearing surface of the insert component when the knee is in 0 degrees of rotation in a varus/valgus direction.

12. A tibial component for a knee joint prosthesis comprising: a platform having an upper surface that includes first and second laterally spaced concavities, each concavity being adapted for receiving one condylar portion of the femoral component and a constraint post for reception in an intercondylar recess of the femoral component, wherein each of the first and second laterally spaced concavities includes a bearing surface that is defined by at least two different radii in a coronal plane, wherein medial and lateral faces of the constraint post further includes a recessed section formed along a lower portion thereof to reduce contact between an inside edge of the femoral component and the constraint post.

13. The tibial component of claim 12, wherein each bearing surface includes a lateral portion and a medial portion, with a radius of the medial portion being less than a radius of the lateral portion.

14. The tibial component of claim 12, wherein the constraint post has a medial face and a lateral face, each of the medial and lateral faces having a curved shape.

15. A knee joint prosthesis comprising: a femoral component having a first condylar bearing surface and a second condylar bearing surface and an intercondytar box; a tibial component; and an insert component associated with the tibial component and having bearing surfaces that are complementary to the first and second condylar bearing surfaces, the insert component including a constraint post for reception within the intercondylar box, wherein the constraint post has a medial face and a lateral face, each of the medial and lateral faces having a curved shape in a coronal plane extending through the constraint post, wherein the curved shape extends superiorly through the constraint post and a portion of each of the medial and lateral faces of the constraint post that is defined by the curved shape contacts walls of the intercondylar box in a varus/valgus rotation, wherein the curvature of each of the medial and lateral faces extends to and terminates at a top of the constraint post, wherein the medial and lateral faces of the constraint post further includes a recessed section formed along a lower portion thereof to reduce contact between an inside edge of the femoral component and the constraint post.

16. The prosthesis of claim 15, wherein each of the first and second condylar bearing surfaces has a convex shape and has a cross-section in a coronal plane that exhibits at least two different radii that define the convex shape of the bearing surface.

17. The prosthesis of claim 15, wherein the medial and lateral faces taper inwardly in a direction toward the top of the constraint post.

* * * * *